US006552020B1

(12) United States Patent
Muller et al.

(10) Patent No.: US 6,552,020 B1
(45) Date of Patent: Apr. 22, 2003

(54) COMPOSITIONS INCLUDING ANTIBIOTICS AND METHODS FOR USING SAME

(75) Inventors: Christopher A. Muller, Foothill Ranch, CA (US); Elizabeth A. Bancroft, Irvine, CA (US); Janet K. Cheetham, Laguna Niguel, CA (US); Harold G. Jensen, Lake Forest, CA (US); Teresa H. Kuan, Placentia, CA (US); David F. Power, Trabuco Canyon, CA (US); Kevin D. Skule, Rancho Santa Margarita, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 09/624,129

(22) Filed: Jul. 24, 2000

Related U.S. Application Data

(63) Continuation-in-part of application No. 09/364,334, filed on Jul. 30, 1999, now abandoned, and a continuation-in-part of application No. 09/365,291, filed on Jul. 30, 1999, now Pat. No. 6,166,012.

(51) Int. Cl.⁷ .............................................. A61K 31/535
(52) U.S. Cl. ...................... 514/235.5; 514/250; 514/912
(58) Field of Search .............................. 514/235.5, 250, 514/912

(56) References Cited

U.S. PATENT DOCUMENTS

| | | |
|---|---|---|
| 4,382,892 A | 5/1983 | Hayakawa et al. |
| 4,454,151 A | 6/1984 | Waterbury |
| 4,551,456 A | 11/1985 | Katz |
| 5,110,493 A | 5/1992 | Cherng-Chyi et al. |
| 5,360,611 A | 11/1994 | Robertson et al. |
| 5,414,011 A | 5/1995 | Fu et al. |
| 5,474,764 A | 12/1995 | Patel et al. |
| 5,811,446 A | 9/1998 | Thomas |
| 5,886,030 A | 3/1999 | Maniar |
| 6,166,012 A | 12/2000 | Muller |

FOREIGN PATENT DOCUMENTS

| | | |
|---|---|---|
| DE | 19729879 | 1/1999 |
| ES | 2065846 | 2/1995 |
| WO | 9902130 | 1/1999 |

OTHER PUBLICATIONS

The Pharmacological Basis of Therapeutics, Gilman et al, pp. 1057–1060, 1990.
O'Callaghan, Cornea, 19(5); 532–537, 1999.

*Primary Examiner*—Zohreh Fay
(74) *Attorney, Agent, or Firm*—Stout, Uxa, Buyan & Mullins, LLP; Frank J. Uxa

(57) ABSTRACT

Compositions including a quinolone component, such as ofloxacin, having fungistatic activity in the compositions, present in an amount effective as an antibiotic when the composition is placed in a mammalian eye, a NSAID component present in an amount to reduce inflammation or pain when the composition is placed in the eye, and a carrier component in an amount effective to act as a carrier for the quinolone component and NSAID component are provided. Methods of using the present compositions, for example, to resolve microbial infections and/or to reduce inflammation and/or pain in a mammalian eye are included within the scope of the present invention. Methods for treating corneal injuries are also included. In addition, methods for treating ocular infections, for example, corneal infections, are included.

34 Claims, No Drawings

US 6,552,020 B1

COMPOSITIONS INCLUDING ANTIBIOTICS AND METHODS FOR USING SAME

RELATED APPLICATION

This application is a continuation-in-part of application Ser. No. 09/364,334 filed Jul. 30, 1999, now abandoned and application Ser. No. 09/365,291, filed Jul. 30, 1999, now U.S. Pat. No. 6,166,012 the disclosure of each of which is hereby incorporated in its entirety herein by reference.

BACKGROUND OF THE INVENTION

The present invention relates to compositions including antibiotics and to methods for using such compositions. More particularly, the invention relates to compositions including antibiotics which have added protection against fungal contamination, which reduce inflammation or pain and/or which are useful in the treatment of corneal ulcers.

Various antibiotic components have been used in ocular applications, for example, to control or manage or prevent ocular infections and the like. Moreover, antibiotic components, such as tobramycin have been suggested for use in combination with other materials, such as ophthalmically acceptable non-steroidal anti-inflammatory drugs or NSAIDs. See, for example, Fu et al. U.S. Pat. No. 5,414,011, the disclosure of which is incorporated in its entirety herein by reference. Quinolones, such as ofloxacin, have been used in compositions for treating ocular infections. These antibiotic compositions include one or more additional components which act as preservatives, for example, benzalkonium chloride (BAK) or organomercurials.

Antibiotic compositions, even with preservatives, have been susceptible to microbial, for example, fungal, contamination. In addition, preservatives tend to cause irritation, allergic reactions, and/or other detrimental side effects when the preserved composition is administered to a patient.

Thus, it would be advantageous to provide antibiotic compositions, and methods for using such compositions, which have added protection against microbial contamination and/or which include relatively reduced concentrations of preservatives.

Corneal injuries, such as corneal ulcers and other corneal conditions which are infected or if left untreated are likely to become infected, are quite painful and sometimes require lengthy periods of time to heal. It would be advantageous to provide compositions and methods effective to reduce the pain of these corneal injuries, for example, while such injuries are healing.

SUMMARY OF THE INVENTION

New antibiotic compositions, for example, for use in mammalian eyes, preferably human eyes, and methods for using such compositions have been discovered. By administering present compositions to humans or animals, for example, to the eyes of humans or animals, desired therapeutic effects are provided, such as the prevention, control or management or substantial elimination of ocular microbial infections, reductions in inflammation and/or pain, reductions in pain caused by corneal injuries and the like.

The present compositions preferably have added protection against microbial, for example, fungal contamination. This feature provides added assurance to the user that the present compositions are free of detrimental microbial contamination. This feature may allow reduced concentrations of preservatives to be included in the present compositions, thereby advantageously reducing detrimental side effects caused by such preservatives when the compositions are administered to patients. The present compositions can be easily produced, for example, using conventional techniques and can be conveniently used, for example, employing conventional methods of administration.

In accordance with one aspect of the invention, the compositions comprise a quinolone component, a NSAID component and a carrier component. The quinolone component is present in an amount effective as a antibiotic when the composition is placed in a mammalian eye. In one useful embodiment, the quinolone component in the composition has fungistatic activity. That is, the quinolone components in the present compositions have sufficient anti-fungal properties or activity to substantially prevent increases in populations of fungi in such compositions. In effect, the present quinolone components act as effective preservatives against fungal growth or contamination in the present compositions. The fungistatic activity of the presently useful quinolone components in the present compositions provide benefits, for example, as described elsewhere herein, which are surprising and substantial. The NSAID component is present in an amount effective to reduce at least one of inflammation and pain when the composition is placed in a mammalian eye. The carrier component is present in an amount effective to act as a carrier for the quinolone component and the NSAID component in the composition, and preferably is ophthalmically acceptable.

The present compositions preferably include a quinolone component which is halogenated, more preferably fluorinated. Very useful compositions and results are obtained when the quinolone component is an ofloxacin component.

Although any NSAID component may be used, the NSAID components included in the present compositions preferably are carboxylic (—COOH) group-containing NSAID components. More preferably, the NSAID component is a pyrrolo pyrrole component, still more preferably a ketorolac component.

The present carrier components may contain one or more pharmaceutically or ophthalmically acceptable ingredients, for example, tonicity adjuster components, buffer components, viscosity components, lubricating components, surfactant components, preservative components and the like, conventionally used, for example, in ophthalmic formulations. Preferably, the compositions have pH's in the physiological range of human beings, for example, in the range of about 4 to about 8.5.

The present compositions may be in any form suitable for effective administration to the human or animal to be treated. Preferably, the compositions are present in a form selected from solutions, suspensions, gels, ointments solids and the like which are very effective for ocular administration. The carrier component may conveniently be selected and/or compounded to provide the composition in the form desired.

Methods of using these compositions are included in the scope of the present invention. Such methods comprise administering to a human or animal, preferably to a mammalian eye, a therapeutically effective amounts of the compositions as described herein. Such methods provide one or more benefits to the human or animal treated in accordance with the present methods. For example, such benefits include prevention, control or management of microbial infections, and reduction in inflammation and/or pain.

In another aspect of the present invention, methods for treating corneal injuries are provided. As used herein, the term "corneal injury" refers to an injury of the cornea which is infected by harmful and/or unwanted microorganism or which, if left untreated is likely to become so infected, for example, before this injury heals. A corneal ulcer is an example of a corneal injury. Such methods comprise administering to a mammalian eye having a corneal injury a therapeutically effective amount of a composition comprising a quinolone component in an amount effective as an antibiotic in the mammalian eye and a NSAID component in an amount effective, in combination with the quinolone component, to provide a reduction in pain caused by the corneal injury. Such reduction in pain, together with the antibiotic effectiveness of the presently useful compositions, reduces the discomfort to the patient resulting from the corneal injury and facilitates or promotes the healing of the injury. The present useful compositions preferably include a carrier component in an amount effective to act as a carrier for the quinolone component and the NSAID component in the presently useful composition.

In another aspect of the present invention, methods for treating ocular infections, such as corneal infections and the like, are provided. Such methods comprise administering to a mammalian eye having an infection caused by one or more microbes or pathogens a therapeutically effective amount of a composition comprising a quinolone component in an amount effective as an antibiotic in the mammalian eye and an effective amount of a NSAID component. In one embodiment, the NSAID component is present in an amount effective to reduce the time needed to eliminate the infection relative to identically administering a similar composition without the NSAID component. The administering step preferably is effective to at least inhibit the offending microbe(s) or pathogen(s) from adhering to a surface of the mammalian eye and/or to inhibit colonization of the offending microbe(s) or pathogen(s) in the mammalian eye.

Any and all features described herein and combinations of such features are included within the scope of the present invention provided that the features of any such combination are not mutually inconsistent.

These and other aspects and advantages of the present invention are set forth in the following detailed description and Examples and claims.

DETAILED DESCRIPTION

The present compositions comprise quinolone components, NSAID components and carrier components.

Preferably, the present quinolone components exhibit fungistatic properties in the present compositions. That is, the quinolone components in the present compositions preferably are effective to preserve the present compositions against population growth of fungi, such as *C. Albicans* and *A. niger*.

The fungistatic activity or properties of the present quinolone components provide added protection against microbial, for example, fungal, contamination of the present compositions. Such fungistatic activity can result in reducing the concentration of added preservative components in the present compositions, thereby reducing the risk of irritation and/or other uncomfortable side effects caused by the presence of such added preservatives. Even if the present compositions are substantially free of added preservative components, it has been found that many of the present compositions have sufficient preservative efficacy to meet or exceed the standards of the United States Preservative Efficacy Test (USPET).

The present compositions include quinolone components. A number of such quinolone components are known and have been used for many years in antibiotic applications. For example, nalidixic acid has been available for the treatment of urinary tract infections. The useful quinolone components preferably are four-quinolones that contain a carboxylic moiety in the three position of the basic structure shown below:

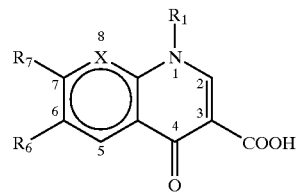

The present quinolone components preferably are halogenated. For example, a chlorinated quinolone component, such as 9-chloro-3-methyl-10-(4-methyl-1-piperazinyl)-7-oxo-2, 3-dihydro-7H-pyridol[1,2,3-de][1, 4]benzozaxine-6 carboxylic acid may be used.

More preferably, the present quinolone components are fluorinated. Examples of such fluorinated quinolones include norfloxacin, ciprofloxacin and ofloxacin. Such fluorinated quinolone components are highly effective against a range of bacteria and are useful in treating various microbial infections in the mammalian eye. Prior ofloxacin-containing compositions including such quinolone used for this purpose include additional preservatives, for example, BAK.

It has been found that the present quinolone components, such as ofloxacin, have sufficient fungistatic activity to be useful in the present compositions to act as a preservative against fungal contamination.

The present compositions include an antibiotically effective amount of the quinolone component. Such amounts may vary over a relatively broad range depending, for example, on the specific form of the composition being used, the specific quinolone component being used, the specific application for the composition, the frequency of use of the composition and the like factors. In many situations, the present compositions may include a quinolone component in an amount in a range of about 0.03% (w/v) or less to about 3% (w/v) or more. Preferably, the present compositions include the quinolone component in an amount in the range of about 0.15% (w/v) to about 0.5% (w/v) or about 1.1% (w/v).

The quinolone component may be any quinolone derivative which is acceptable or suitable for administration to the eye and has at least a portion, preferably a major portion or at least about 50% of the antibiotic effectiveness of the basic quinolone in the present composition in the mammalian eye. The present quinolone component may be selected from the quinolone itself or quinolone hydrates or ophthalmically acceptable salts of such quinolones, for example, including acid addition salts such as hydrochlorides, maleates, pamoates and the like, and alkali metal salts such as sodium and potassium salts, and mixtures thereof and the like.

The present compositions include a NSAID component in an amount effective to reduce inflammation and/or pain when the compositions are administered to a mammalian eye, for example, to prevent or treat diseases which are either caused by, associated with or accompanied by inflammatory processes and/or pain, including, among others, glaucoma, cystoid macular edema, uveitis, diabetic retinopathy and conjunctivitis, or any trauma caused by eye surgery or eye injury.

The NSAID component may or may not include a carboxylic (—COOH) group or moiety, or a carboxylic derived group or moiety. In one embodiment, the NSAID component inhibits the cyclo-oxygenase enzyme, which has two (2) isoforms, referred to as COX-1 and COX-2. Many of the well known NSAID components are basiclaly non-selective COX inhibitors. NSAID components which are selective COX-2 inhibitors are also known. Both types of NSAID components, that is both non-selective COX inhibitors and selective COX-2 inhibitors are useful in accordance with the present invention. The NSAID component may be selected from phenylalkanoic acids, such as diclofenac, flurbiprofen, ketorolac, piroxicam and the like; indoles, such as indomethacin and the like; diarylpyrazoles, such as celecoxib and the like; pyrrolo pyrroles; and other agents that inhibit prostaglandin synthesis. A very useful NSAID component is the pyrrolo pyrrole which has a propionic acid moiety, known as ketorolac and derivatives thereof, such as non-toxic esters and salts thereof. Pyrrolo pyrroles have been suggested for use in the treatment of certain ophthalmic diseases in Waterbury U.S. Pat. No. 4,454,151, the disclosure of which is incorporated in its entirety herein by reference.

The NSAID component may be present in the present compositions in any suitable concentration effective to reduce inflammation or pain when the composition is placed in a mammalian eye. The NSAID component preferably is present in an amount in a range of about 0.001% (w/v) or less to about 10% (w/v) or more, and more preferably in a range of about 0.02% (w/v) to about 0.5% (w/v) or about 1% (w/v).

The present carrier components may be selected from pharmaceutically acceptable organic and/or inorganic components which, preferably, in the present compositions are ophthalmically acceptable. As used herein, the term "ophthalmically acceptable" refers to a material which, at the concentration or amount in question, is compatible with ocular tissue, that is the material does not cause significant or undue detrimental effects when brought into contact with ocular tissue. The carrier component preferably is ophthalmically acceptable. Preferably, each component of the present compositions is also compatible with the other components of the compositions.

Examples of suitable materials useful in the present carrier components include water, mixtures of water and water-miscible solvents such as lower alkanols or aralkanols, vegetable oils, polyalkylene glycols, petroleum-based jelly, ethyl cellulose, ethyl oleate, carboxymethyl cellulose, polyvinylpyrrolidone, isopropyl mirstate, other conventionally employed pharmaceutically acceptable materials and the like.

The carrier component may also include auxiliary substances such as emulsifiers, wetting agents, bodying agents, buffer components, acids and/or bases, tonicity adjuster components, surfactant components, viscosity agents, lubricity components, preservative components, other materials useful in ophthalmic formulations and the like, including, but not limited to, such substances which are conventionally used in ophthalmic compositions.

Examples of optionally useful bodying agents include, but are not limited to, various polyethylene glycols, carbowaxes, petroleum jelly and the like.

Suitable buffers include, but are not limited to, inorganic buffers such as phosphate buffers, borate buffers and the like, and organic buffers, such as acetate buffers, citrate buffers, tromethamine and the like.

Tonicity adjusters optionally useful in the present compositions include, but are not limited to, dextrose, potassium chloride and/or sodium chloride and the like, preferably sodium chloride.

Acids optionally useful in the present compositions include boric acid, hydrochloric acid, acetic acid, other acids which are ophthalmically acceptable in the concentrations used, and the like.

Bases which may be included in the present compositions include, but are not limited to, sodium and/or potassium hydroxides, other alkali and/or alkaline earth metal hydroxides, organic bases, other bases which are ophthalmically acceptable in the concentrations used, and the like.

The acid/bases/buffers preferably are included, if at all, to provide and/or maintain the present compositions at a pH in the physiologically acceptable range, more preferably in a range of about 4 to about 8.5, still more preferably about 6 to about 8, and especially about 6.8 to about 8.

Surfactant components optionally useful in the compositions of the present invention include, but are not limited to, lipoprotein detergents that when present in the compositions reduce the surface tension between the compositions and the eye (lacrimal) fluid. Preferably, nonionic surfactants are used.

Viscosity agents optionally useful in the compositions of the present invention include, but are not limited to, cellulose derivatives such as hydroxypropylmethyl cellulose, sodium carboxymethyl cellulose, hydroxyethyl cellulose, other viscosity inducing materials useful in ophthalmic formulations, and the like.

Lubricating components optionally useful in compositions of the present invention include, but are not limited to, polyvinyl alcohol, polyvinylpyrrolidone, carbopol and the like.

Preservative components optionally useful in the compositions of the present invention include, but are not limited to, BAK, organo-mercurials, such as thimerosal and phenylmercuric acetate and nitrate, quaternary ammonium compounds, methyl and propyl parabens, benzl alcohol, phenylethanol and the like. Because of the fungistatic activity of the quinolone components of the present compositions, the concentration of the preservative component, if present at all, in the present compositions may be, and preferably is, reduced, more preferably by at least about 10% or at least about 20%, relative to the concentration of the preservative needed in a similar composition including, in place of the presently useful quinolone component with fungistatic activity, an antibiotic component without such fungistatic activity and still be effectively preserved, for example, adequately preserved to pass the applicable United States and/or European preservative efficacy tests.

The present compositions may include effective amounts of chelating or sequestering components, such as ethylene diamine tetraacetic acid (EDTA), citric acid, tartaric acid and the like.

Other optional excipients useful in the present compositions include stabilizing agents such as antioxidants, for example, alkali metal metabisulfates, ascorbic acid and the like.

The carrier component may be in various forms. In one embodiment, the carrier component comprises a liquid, and the composition may be a solution or a suspension. In either situation, the carrier may simply contain water and one or more auxiliary components noted elsewhere herein.

The present compositions may be in any suitable form effective to be administered to the eye. Such forms include solutions, suspensions, ointments, gels, solids and the like. An ointment may be considered as a form intermediate between a suspension and a gel. Each of these forms of the present compositions can be prepared using techniques and processing which are conventional and well known in the art.

In another embodiment, the carrier component may be in the form of a clear material which forms a semi-solid "gel" at human body temperatures. Various polymers, many of which are conventional and well known in the art, can be included in the carrier components to provide the present compositions in the form of gels. For example, a polymer system including alkylene diamine tetra substituted with about 40% to about 80% poly(oxyethylene) units and about 20% to about 60% poly(oxypropylene) units may be employed. The molecular weight of the polymer used preferably is at least about 7,000 and can be as high as about 50,000, more preferably in the range of about 7,000 to about 30,000. The gel forming component, if any is present in an amount effective to provide the composition in the form of a gel. For example, such gel forming component may be present in an amount in a range of about 10% or less to about 50% or more by weight of the total carrier component.

The compositions may also be in the form of solid inserts, for example a solid dosage form that is suitable for insertion into the cul-de-sac of a mammalian eye. To this end, the composition components can be included with is a non-bioerodible insert, for example, one which after dispensing the active component or components remains essentially intact, or a bio-erodible insert, for example, one that either is soluble in lacrimal fluids, or otherwise disintegrates.

A solid water soluble polymer may be employed in the carrier component. Such polymers include, for example, cellulose derivatives such as methylcellulose, sodium carboxymethyl cellulose, or a hydroxy lower alkyl cellulose such as hydroxyethyl cellulose, hydroxypropyl cellulose, hydroxypropylmethyl cellulose and the like; acrylates such as polyacrylic acid salts, ethyl acrylates, polyacrylamides, natural products such as gelatin, alginates, pectins, tragacanth, daraya, chondrus, agar, acacia; the starch derivatives such as starch acetate, hydroxyethyl starch ethers, hydroxypropy starch, as well as other synthetic derivatives such as polyvinyl alcohol, polyvinyl pyrrolidone, polyvinyl methyl ether, polyethylene oxide, neutralized carbopol and xanthan gum, mixtures thereof and the like.

The present compositions may be prepared using conventional techniques, for example, by formation of solutions, gels, suspensions, etc., using well known and conventional techniques. For a more detailed discussion of the preparation and administration of ophthalmic formulations see *Remingtons Pharmaceutical Sciences*, 15 Ed., Pgs. 1489 to 1504 (1975) which is incorporated in its entirety herein by reference.

In general, the present methods for treating mammalian eyes comprise administering to the mammalian eye a therapeutically effective amount of the present composition thereby providing an effective antibiotic in the mammalian eye and reducing inflammation and/or pain in the mammalian eye.

Methods for treating corneal injuries, such as corneal ulcers, are also included within the scope of the present invention. Such methods comprise administering to a mammalian, preferably human, eye having a corneal injury a therapeutically effective amount of a composition comprising a quinolone component in an amount effective as an antibiotic in the mammalian eye and a NSAID component in an amount effective, in combination with the quinolone component, to provide a reduction in pain caused by the corneal injury. Such reduction in pain, together with the antibiotic effectiveness of the presently useful compositions reduces the discomfort to the patient resulting from the corneal injury and facilitates or promotes the healing of the injury. Corneal injuries include, but are not limited to, abrasions, lacerations, scratches, surgical trauma, accidental or incidental trauma, bruises and the like to the cornea which are infected or are likely to become infected which cause pain to the mammal.

The present useful corneal injury-treating compositions preferably include a carrier component in an amount effective to act as a carrier for the quinolone component and the NSAID component in the presently useful compositions.

The quinolone components, NSAID components and carrier components useful in treating corneal injuries preferably are as described elsewhere herein. The presently useful compositions can be in any suitable form effective to treat the corneal injury, preferably in a form as described elsewhere herein.

Methods for treating ocular infections, such as corneal infections, are also included within the scope of the present invention. Such infections are caused by the presence of one or more microbes or pathogens in or on the eye in an amount or quantity to detrimentally affect the eye, for example, causing irritation, inflammation, redness, pain, tissue damage and the like. Examples of such infections include, but are not limited to, keratitis, such as bacterial keratitis, as well as bacterial conjunctivitis and the like infections. The present infection treating methods comprise administering to a mammalian, preferably human, eye having an infection caused by one or more microbes or pathogens a therapeutically effective amount of a composition comprising a quinolone component in an amount effective as an antibiotic in the mammalian eye and an effective amount of a NSAID component.

In one embodiment, the NSAID component is effective to reduce the time needed to eliminate the infection relative to identically administering a similar composition without the NSAID component. In addition, or alternately, the administering step, and preferably the NSAID component used in the administering step, is effective to at least inhibit the one or more microbes or pathogens causing the infection from adhering to a surface of the eye. In a very useful embodiment, the administering step, and preferably the NSAID component used in the administering step, is effective to at least inhibit, or even substantially prevent, colonization of the one or more microbes or pathogens in the eye.

The presently useful ocular infection-treating compositions preferably include a carrier component in an amount effective to act as a carrier for the quinolone component and the NSAID component in the presently useful compositions.

The quinolone components, NSAID components and carrier components useful in treating ocular infections preferably are as described elsewhere herein. The presently useful compositions can be in any suitable form effective to treat the ocular infection, preferably in a form as described elsewhere herein.

The present use methods may be considered to be curative and/or preventative when applied, presurgically or immediately post traumatically, that is before a microbial infection develops, or before inflammation and/or pain and/or infection is apparent. The present use methods are effective to reduce the risk of the formation of such infections and to reduce the severity of any inflammation or pain which may develop.

The present methods of use, including the general methods of use, the methods of treating corneal ulcers and the methods of treating ocular infections, may involve any suitable administration step or steps to provide an effective amount of the composition to the mammalian eye. Such administering may include, but is not limited to, topical application to the eye, instillation into the eye, placing an insert into the cul-de-sac (space) between the eyeball and the eyelid and the like. Other conventional methods of administering compositions to the eye may be employed provided that the compositions are administered so as to provide the benefits desired.

The dosage level of the composition depends, of course, on many factors, for example, the particular application involved, the particular active components employed, the concentration of the active components in the composition, the severity of the infection/ inflammation/pain/corneal ulcer and the individual's response to the treatment. Such dosage can be easily determined by routine and well known techniques to achieve the desired results in the individual patient being treated.

The following non-limiting examples illustrate certain aspects of the present invention.

EXAMPLES 1 TO 11

A series of compositions, Compositions 1 to 11, are prepared by blending various components together. These compositions have the following chemical make-ups.

| Composition 1 | |
|---|---|
| Ofloxacin | 0.6 w/v % |
| NaCl | 0.79 w/v % |
| pH | 6.4 |
| water | q.s. 100% |
| Composition 2 | |
| Ofloxacin | 1.0 w/v % |
| NaCl | 0.79 w/v % |
| pH | 6.4 |
| water | q.s. 100% |
| Composition 3 | |
| Ofloxacin | 0.6 w/v % |
| NaCl | 0.3 w/v % |
| EDTA | 0.1 wt % |
| Boric Acid | 1.0 w/v % |
| pH | 6.4 |
| water | q.s. 100% |
| Composition 4 | |
| Ofloxacin | 1.0 w/v % |
| NaCl | 0.3 w/v % |
| EDTA | 0.1 w/v % |
| Boric Acid | 1.0 w/v % |
| pH | 6.4 |
| water | q.s. 100% |
| Composition 5 | |
| Ketorolac | 0.5 w/v % |
| Ofloxacin | 0.6 w/v % |
| NaCl | 0.79 w/v % |
| pH | 6.4 |
| water | q.s. 100% |

| Composition 6 | |
|---|---|
| Ketorolac | 0.5 w/v % |
| Ofloxacin | 1.0 w/v % |
| NaCl | 0.79 w/v % |
| pH | 6.4 |
| water | q.s. 100% |
| Composition 7 | |
| Ketorolac | 0.5 w/v % |
| Ofloxacin | 0.6 w/v % |
| NaCl | 0.3 w/v % |
| EDTA | 0.1 w/v % |
| Boric Acid | 1.0 w/v % |
| pH | 6.4 |
| water | q.s. 100% |
| Composition 8 | |
| Ketorolac | 0.5 w/v % |
| Ofloxacin | 1.0 w/v % |
| NaCl | 0.3 w/v % |
| EDTA | 0.1 w/v % |
| Boric Acid | 1.0 w/v % |
| pH | 6.4 |
| water | q.s. 100% |
| Composition 9 | |
| Ketorolac | 0.5 w/v % |
| Ofloxacin | 0.3 w/v % |
| NaCl | 0.79 w/v % |
| BAK | 0.005 w/v % |
| L-Arginine | 0.28 w/v % |
| pH | 6.4 |
| water | q.s. 100% |
| Composition 10 | |
| Ketorolac | 0.5 w/v % |
| Ofloxacin | 0.3 w/v % |
| NaCl | 0.79 w/v % |
| BAK | 0.005 w/v % |
| METHOCEL ®[(1)] | 0.1 w/v % |
| Carbopol[(2)] | 0.2 w/v % |
| pH | 6.4 |
| water | q.s. 100% |
| Composition 11 | |
| Ofloxacin | 0.3 w/v % |
| BAK | 0.005 w/v % |
| METHOCEL ®[(1)] | 0.1 w/v % |
| Carbopol[(2)] | 0.225 w/v % |
| Glycerine | 2.6 w/v % |
| pH | 6.5 |
| water | q.s. 100% |

[(1)]Methyl cellulose
[(2)]One of a series of polymers of 2-propenoic acid cross-linked with alkyl ethers of pentoerythritol.

An abbreviated preservative efficacy test of each of these compositions is performed using *S. aureus* ATCC 6538 and *A. niger* ATCC 16404 as the test organisms. The compositions are tested against Ph Eur-A/B and USP criteria according to ARM T-005. Ten (10) milliliter of each composition is challenged with approximately $10^5$ cfu/ml of test organism. At the appropriate time intervals, the amount of bacterial and fungal survivors are assayed using Dey Engley broth (DE) as the neutralizer media. DE, along with filtration, is sufficient at neutralizing the antimicrobial agents in the compositions. One (1) ml of each sample is diluted into nine (9) ml of DE. One (1) of the 1:10 dilution is filtered through a 0.45 µm filter and washed with 100 ml saline/TWEEN® 80. After washing the filter a second time with 100 ml of a saline/TWEEN® 80 solution, the filtrate is placed onto a TSA plate for bacteria and SAB for fungi. The same procedure as stated above was followed for composition 11 (which is in the form of a gel) except a 1:100 dilution of the product is made prior to filtration (0.1 ml of product is added to 10 ml DE).

A summary of the results of these preservative efficacy tests is as follows:

| Composition | USP | Ph Eur-A | Ph Eur-B |
|---|---|---|---|
| 1 | PASS | FAIL | Marginal PASS |
| 2 | PASS | FAIL | FAIL |
| 3 | PASS | FAIL | Marginal PASS |
| 4 | PASS | FAIL | PASS |
| 5 | PASS | FAIL | FAIL |
| 6 | PASS | FAIL | FAIL |
| 7 | PASS | PASS | Marginal PASS |
| 8 | PASS | FAIL | PASS |
| 9 | PASS | PASS | PASS |
| 10 | PASS | PASS | PASS |
| 11 | PASS | PASS | PASS |

Detailed results of the preservative efficacy tests were as follows:

| Test Organism Inoculum level | Test Interval | \multicolumn{11}{c}{Compositions} | | | | | | | | | | |
|---|---|---|---|---|---|---|---|---|---|---|---|
| | | 1 | 2 | 3 | 4 | 5 | 6 | 7 | 8 | 9 | 10 | 11 |
| S. aureus ATTC 6538 $4 \times 10^5$ | 6 hours | $2 \times 10^5$ | $9 \times 10^4$ | $1 \times 10^5$ | $8 \times 10^4$ | $8 \times 10^4$ | $1 \times 10^5$ | $1 \times 10^5$ | $1 \times 10^5$ | <10 | <10 | <10 |
| | 24 hours | $7 \times 10^4$ | $3 \times 10^4$ | $6 \times 10^4$ | <10 | $8 \times 10^3$ | $2 \times 10^3$ | $3 \times 10^3$ | $1 \times 10^4$ | <10 | <10 | <10 |
| | 7 days | <10 | <10 | <10 | $1 \times 10^1$ | <10 | <10 | <10 | <10 | <10 | <10 | <10 |
| | 14 days | <10 | <10 | <10 | <10 | <10 | <10 | <10 | <10 | <10 | <10 | <10 |
| | 28 days | <10 | <10 | <10 | <10 | <10 | <10 | <10 | <10 | <10 | <10 | <10 |
| A. niger ATCC 16404 $1 \times 10^5$ | 7 days | $8 \times 10^4$ | $8 \times 10^4$ | $4 \times 10^3$ | $1 \times 10^3$ | $7 \times 10^4$ | $7 \times 10^4$ | $2 \times 10^4$ | $3 \times 10^3$ | $1 \times 10^1$ | <10 | $1 \times 10^1$ |
| | 14 days | $2 \times 10^4$ | $3 \times 10^4$ | $2 \times 10^3$ | $1 \times 10^3$ | $9 \times 10^4$ | $9 \times 10^4$ | $2 \times 10^4$ | $7 \times 10^3$ | <10 | <10 | <10 |
| | 28 days | $1 \times 10^4$ | $3 \times 10^4$ | $2 \times 10^3$ | $8 \times 10^2$ | $2 \times 10^4$ | $1 \times 10^4$ | $4 \times 10^2$ | $1 \times 10^2$ | <10 | <10 | <1 |

All of the compositions very effectively pass the USPET. In particular, the fact that Compositions 1 to 8, which include no component known to be effective as a preservative, pass the USPET is surprising, especially since prior art compositions which have included a quinolone, such as ofloxacin, have included preservatives, such as BAY. In addition, Compositions 1 to 8 have sufficient antifungal activity to prevent A. niger from increasing in population. Thus, the quinolone, ofloxacin, included in these compositions has sufficient fungistatic activity to act as a preservative for the composition against A. niger contamination.

EXAMPLES 12 TO 23

A further series of compositions, Compositions 12 to 24, are prepared by blending various components together. These compositions have the following chemical make-ups. Each composition included sufficient water to total 1000 by weight.

| EXAMPLE NO. | ACTIVES | CONCENTRATION, w/v % |
|---|---|---|
| 12 | Ketorolac | 0.5 |
| | Ofloxacin | 0.3 |
| | NaCl | 0.79 |
| | pH | 6.4 |
| 13 | Ketorolac | 0.5 |
| | Ofloxacin | 0.3 |
| | NaCl | 0.30 |
| | EDTA | 0.1 |
| | Boric Acid | 1.0 |
| | pH | 6.4 |
| 14 | Ketorolac | 0.5 |
| | Ofloxacin | 0.3 |
| | NaCl | 0.79 |
| | BAK | 0.005 |
| | pH | 6.4 |
| 15 | Ketorolac | 0.5 |
| | Ofloxacin | 0.3 |
| | NaCl | 0.79 |
| | pH | 7.4 |
| 16 | Ketorolac | 0.5 |
| | Ofloxacin | 0.3 |
| | NaCl | 0.79 |
| | BAK | 0.005 |
| | pH | 7.6 |
| 17 | Ketorolac | 0.5 |
| | Ofloxacin | 0.3 |
| | NaCl | 0.79 |
| | BAK | 0.005 |
| | Octoxynol[3] | 0.007 |
| | pH | 6.4 |
| 18 | Ketorolac | 0.5 |
| | Ofloxacin | 0.3 |
| | NaCl | 0.79 |
| | BAK | 0.005 |
| | Octoxynol[3] | 0.007 |
| | pH | 7.6 |
| 19 | Ketorolac | 0.5 |
| | Ofloxacin | 0.3 |
| | NaCl | 0.79 |
| | BAK | 0.005 |
| | Cyclodextrin[4] | 0.1 |
| | pH | 6.4 |
| 20 | Ketorolac | 0.5 |
| | Ofloxacin | 0.5 |
| | NaCl | 0.79 |
| | BAK | 0.005 |
| | Cyclodextrin[4] | 0.1 |
| | pH | 7.6 |
| 21 | Ketorolac | 0.5 |
| | Ofloxacin | 0.3 |
| | NaCl | 0.79 |
| | Purite[5] | 0.007 |
| | pH | 7.6 |

-continued

| EXAMPLE NO. | ACTIVES | CONCENTRATION, w/v % |
|---|---|---|
| 22 | Ketorolac | 0.5 |
| | Ofloxacin | 0.3 |
| | NaCl | 0.79 |
| | Purite[5] | 0.007 |
| | Octoxynol[3] | 0.007 |
| | pH | 7.6 |
| 23 | Ketorolac | 0.5 |
| | Ofloxacin | 0.3 |
| | NaCl | 0.79 |
| | Purite[5] | 0.007 |
| | Cyclodextrin[4] | 0.1 |
| | pH | 7.6 |

[3]polyethylene glycol mono (octylphenyl) ether
[4]7-sulfobutylether-beta-cyclodextrin
[5]Stabilized chlorine dioxide The samples were tested for preservative efficacy against Ph Eur-A/B and USP criteria according to ARM T-005. Ten (10) milliliters of each sample was challenged with approximately $10^5$ cfu/ml of test organism. The test organisms included *S. aureus* ATCC 6538, *P. aeruginosa* ATCC 9027, *E. coli* ATCC 8739, *C. albicans* ATCC 10231, and *A. niger* ATCC 16404. At the appropriate time intervals, the amount of bacterial and fungal survivors were assayed using DE as the neutralizer media. DE, along with filtration, is sufficient at neutralizing the antimicrobial agents in the compositions. One (1) ml of each sample was diluted into 9 ml of DE. The whole 10 ml was filtered through a 0.45 um filter and washed with 100 ml of phosphate buffered saline pH 5.4. After washing the filter a second time with 100 ml phosphate buffered saline/TWEEN® 80, the filter was placed onto a blood agar plate for bacteria and SAB for fungi.

The results are summarized in the below table.

| SAMPLE ID | USP | Ph Eur-A | Ph Eur-B |
|---|---|---|---|
| 12 | PASS | FAIL | FAIL |
| 13 | PASS | FAIL | FAIL |
| 14 | PASS | PASS | PASS |
| 15 | PASS | FAIL | FAIL |
| 16 | PASS | PASS | PASS |
| 17 | PASS | PASS | PASS |
| 18 | PASS | PASS | PASS |
| 19 | PASS | FAIL | PASS |
| 20 | PASS | PASS | PASS |
| 21 | PASS | FAIL | FAIL |
| 22 | PASS | FAIL | FAIL |
| 23 | PASS | FAIL | FAIL |

Detailed results of the preservation efficacy tests on Compositions 12 to 17 were as follows:

| Test Organism | | Composition | | | | | |
|---|---|---|---|---|---|---|---|
| Inoculum level | Test Interval | 12 | 13 | 14 | 15 | 16 | 17 |
| *S. aureus* | 6 hours | $2 \times 10^5$ | $2 \times 10^5$ | 4 | $3 \times 10^5$ | <10 | 1 |
| ATTC 6538 | 24 hours | $2 \times 10^5$ | $2 \times 10^5$ | <10 | $3 \times 10^5$ | <10 | <10 |
| $5 \times 10^5$ | 7 days | <10 | $2 \times 10^1$ | <10 | <10 | <10 | <10 |
| | 14 days | <10 | <10 | <10 | <10 | <10 | <10 |
| | 28 days | <10 | <10 | <10 | <10 | <10 | <10 |
| *P. aeruginosa* | 6 hours | <10 | <10 | <10 | <10 | <10 | <10 |
| ATCC 9027 | 24 hours | <10 | <10 | <10 | <10 | <10 | <10 |
| $3 \times 10^5$ | 7 days | <10 | $2 \times 10^1$ | <10 | <10 | <10 | <10 |
| | 14 days | <10 | <10 | <10 | <10 | <10 | <10 |
| | 28 days | <10 | <10 | <10 | <10 | <10 | <10 |
| *E. coli* | 6 hours | $6 \times 10^1$ | $5 \times 10^1$ | <10 | $5 \times 10^1$ | <10 | <10 |
| ATCC 8739 | 24 hours | $5 \times 10^2$ | <10 | <10 | <10 | <10 | <10 |
| $5 \times 10^5$ | 7 days | <10 | <10 | <10 | <10 | <10 | <10 |
| | 14 days | <10 | <10 | <10 | <10 | <10 | <10 |
| | 28 days | <10 | <10 | <10 | <10 | <10 | <10 |
| *C. albicans* | 7 days | $1 \times 10^5$ | $2 \times 10^5$ | <10 | $3 \times 10^5$ | <10 | <10 |
| ATCC 10231 | 14 days | $1 \times 10^5$ | $2 \times 10^5$ | <10 | $1 \times 10^5$ | <10 | <10 |
| $3 \times 10^5$ | 28 days | $8 \times 10^4$ | $9 \times 10^4$ | <10 | $9 \times 10^4$ | <10 | <10 |
| *A. niger* | 7 days | $6 \times 10^4$ | $6 \times 10^4$ | $3 \times 10^1$ | $7 \times 10^4$ | <10 | $3 \times 10^1$ |
| ATCC 16404 | 14 days | $4 \times 10^4$ | $3 \times 10^4$ | 4 | $6 \times 10^4$ | $1 \times 10^2$ | <10 |
| $1 \times 10^5$ | 28 days | $3 \times 10^4$ | $3 \times 10^4$ | <10 | $4 \times 10^4$ | <10 | <10 |

All of the Compositions pass the USPET. Compositions 12 15, include no component known to be effective as a preservative. Although Compositions 12 and 15 do not pass the European Preservative Efficacy Tests, they do have sufficient antifungal activity to prevent *C. albicans* and *A. niger* from increasing in population. The quinolone, ofloxacin, included in these compositions has sufficient fungistatic activity to act as a preservative for the composition against *C. albicans* and *A. niger* contamination.

EXAMPLES 24 TO 41

Compositions 5 to 10 and 12 to 23 are each administered to a human eye which has been subjected to surgical trauma.

Before administration, each eye exhibits a degree of inflammation and is the source of a degree of pain.

Each composition which is a solution is administered to the eye in an amount of about 1 to 2 drops per eye with the drops containing about 25 to 50 micro liters. The drops are administered 3 to 4 times per day. Each composition which is a gel is administered by placing about 50 to 100 micro liters of the composition between the eye lid and the eye ball 3 to 4 times a day.

After a week of such administering, each of the eyes treated exhibits no inflammation and is not a source of pain. In addition, each of the eyes has remained free of microbial infection.

EXAMPLES 42 TO 59

Compositions 5 to 10 and 12 to 23 are each administered to a human eye which has a corneal ulcer. Before administration, each eye is the source of a substantial degree of pain.

Each composition which is a solution is administered to the eye in an amount of about 1 to 2 drops per eye with the drops containing about 25 to 50 micro liters. The drops are administered every 30 minutes. Each composition which is a gel is administered by placing about 50 to 100 micro liters of the composition between the eye lid and the eye ball every 30 minutes.

Within one day after the initial administering, the pain resulting from each of the corneal ulcers is substantially eliminated. After two weeks of such administering, each of the corneal ulcers has substantially completely healed and no pain from the ulcer is experienced. In addition, each of the eyes has remained free of microbial infection.

EXAMPLES 60 TO 78

Compositions 5 to 10 and 12 to 23 are each administered to a human eye which has a corneal microbial infection.

Each composition which is a solution is administered to the eye in an amount of about 1 to 2 drops per eye with the drops containing about 25 to 50 micro liters. The drops are administered every 30 minutes. Each composition which is a gel is administered by placing about 50 to 100 micro liters of the composition between the eye lid and the eye ball every 30 minutes.

After a period of time, on the order of from about 4 days to about 14 days, of such administering, each of the corneal microbial infections has been substantially completely eliminated and no pain from the infection is experienced. Using such compositions to treat these ocular infections, a reduced time period of administering the compositions is needed to substantially completely eliminate the infection relative to similar compositions without the NSAID component, ketorolac. The NSAID component is believed to inhibit the colonization of the microbes or pathogens causing the ocular infections. For example, the NSAID component in the composition administered may inhibit or substantially prevent the offending microbes or pathogens from adhering to one or more surfaces of the eye, thereby inhibiting the spread or progress of the infection. The infection is resolved or eliminated more quickly using the present quinolone, NSAID-containing compositions relative to using similar compositions without the NSAID component.

While this invention has been described with respect to various specific examples and embodiments, it is to be understood that the invention is not limited thereto and that it can be variously practiced within the scope of the following claims.

What is claimed is:

1. A method for treating an ocular infection comprising: administering to a mammalian eye having an infection caused by one or more pathogens a therapeutically effective amount of a composition comprising quinolone component in an amount effective as an antibiotic in the mammalian eye and a NSAID component in an amount effective to reduce the time needed to eliminate the infection relative to identically administering a similar composition without the NSAID component, the composition being free of other components effective as preservatives, the composition being sufficiently self-preserved so as to pass the United States Preservative Efficacy Test.

2. The method of claim 1 wherein the administering step is effective to inhibit colonization of the one or more pathogens in the mammalian eye.

3. The method of claim 1 wherein the mammalian eye includes a surface and the administering step is effective to at least inhibit the one or more pathogens from adhering to the surface.

4. The method of claim 1 wherein the ocular infection is a corneal infection.

5. The method of claim 3 wherein the administering step is effective to inhibit colonization of the one or more pathogens in the mammalian eye.

6. The method of claim 4 wherein the administering step is effective to at least inhibit the one or more pathogens from adhering to a cornea of the eye.

7. The method of claim 1 wherein the quinolone component is a halogenated quinolone component.

8. The method of claim 1 wherein the quinolone component is a fluorinated quinolone component.

9. The method of claim 1 wherein the quinolone component is an ofloxacin component.

10. The method of claim 1 wherein the NSAID component is a carboxyl group-containing NSAID component.

11. The method of claim 1 wherein the NSAID component is a ketorolac component.

12. The method of claim 9 wherein the NSAID component is a ketorolac component.

13. A method for treating an ocular infection comprising: administering to at least one surface of a mammalian eye having an infection caused by one or more pathogens therapeutically effective amount a composition comprising a quinolone component in an amount effective as an antibiotic in the mammalian eye and a NSAID component in an amount effective to at least inhibit the one or more pathogens from adhering to the surface, the composition being free of other component effective as preservatives, the composition being sufficiently self-preserved so as to pass the United States Preservative Efficacy Test.

14. The method of claim 13 wherein the ocular infection is a corneal infection.

15. The method of claim 13 herein the quinolone component is a halogenated quinolone component.

16. The method of claim 13 wherein the quinolone component is a fluorinated quinolone component.

17. The method of claim 13 wherein the quinolone component is an ofloxacin component.

18. The method of claim 14 wherein the quinolone component is an ofloxacin component.

19. The method of claim 13 wherein the NSAID component is a carboxyl group-containing NSAID component.

20. The method of claim 13 wherein the NSAID component is a ketorolac component.

21. The method of claim 14 wherein the NSAID component is a ketorolac component.

22. The method of claim 17 wherein the NSAID component is a ketorolac component.

23. The method of claim 18 wherein the NSAID component is a ketorolac component.

24. A method for treating an ocular infection comprising:
   administering to a mammalian eye having an infection caused by one or more pathogens a therapeutically effective amount of a composition comprising a quinolone component in an amount effective as an antibiotic in the mammalian eye and a NSAID component in an amount effective to inhibit colonization of the one or more pathogens in the mammalian eye, the compositions being free of other components effective as preservatives, the composition being sufficiently self-preserved so as to pass the United States Preservative Efficacy Test.

25. The method of claim 24 wherein the ocular infection is a corneal infection.

26. The method of claim 24 herein the quinolone component is a halogenated quinolone component.

27. The method of claim 24 wherein the quinolone component is a fluorinated quinolone component.

28. The method of claim 24 wherein the quinolone component is an ofloxacin component.

29. The method of claim 25 wherein the quinolone component is an ofloxacin component.

30. The method of claim 24 wherein the NSAID component is a carboxyl group-containing NSAID component.

31. The method of claim 24 wherein the NSAID component is a ketorolac component.

32. The method of claim 25 wherein the NSAID component is a ketorolac component.

33. The method of claim 28 wherein the NSAID component is a ketorolac component.

34. The method of claim 29 wherein the NSAID component is a ketorolac component.

* * * * *